(12) United States Patent
Hardcastle, III

(10) Patent No.: US 7,454,990 B2
(45) Date of Patent: Nov. 25, 2008

(54) VARIABLY CONTROLLED ACCELERATED WEATHERING TEST APPARATUS

(75) Inventor: Henry K. Hardcastle, III, Phoenix, AZ (US)

(73) Assignee: Atlas Material Testing, LLC, Chicago, IL (US)

( * ) Notice: Subject to any disclaimer, the term of this patent is extended or adjusted under 35 U.S.C. 154(b) by 588 days.

(21) Appl. No.: 11/083,832

(22) Filed: Mar. 18, 2005

(65) Prior Publication Data

US 2006/0207589 A1    Sep. 21, 2006

(51) Int. Cl.
*G01N 17/00* (2006.01)

(52) U.S. Cl. ............... 73/865.6; 250/492.1; 374/45; 374/57

(58) Field of Classification Search ............... 73/865.6; 250/228, 492.1; 356/236, 244; 374/45, 57
See application file for complete search history.

(56) References Cited

U.S. PATENT DOCUMENTS

| | | | |
|---|---|---|---|
| 951,850 A | 3/1910 | Skilling | |
| 2,945,417 A | 7/1960 | Caryl et al. | |
| 3,500,682 A * | 3/1970 | Newfield | 73/150 R |
| 3,521,966 A * | 7/1970 | Archer | 356/256 |
| 3,521,967 A * | 7/1970 | Archer | 356/256 |
| 3,861,379 A * | 1/1975 | Anderson, Jr. | 126/577 |
| 3,889,531 A | 6/1975 | Suga | |
| 4,120,282 A * | 10/1978 | Espy | 126/684 |
| 4,141,626 A * | 2/1979 | Treytl et al. | 359/846 |
| 4,146,785 A * | 3/1979 | Neale | 250/203.4 |
| 4,226,502 A * | 10/1980 | Gunzler | 126/574 |
| 4,316,448 A * | 2/1982 | Dodge | 126/600 |
| 4,536,847 A * | 8/1985 | Erickson et al. | 702/150 |
| 4,597,377 A * | 7/1986 | Melamed | 126/600 |
| 4,604,990 A * | 8/1986 | Nikkel et al. | 126/660 |
| 4,807,247 A | 2/1989 | Robbins, III | |
| 5,153,780 A * | 10/1992 | Jorgensen et al. | 359/853 |
| 5,325,844 A * | 7/1994 | Rogers et al. | 126/605 |
| 5,347,317 A * | 9/1994 | Sakurai | 348/511 |
| 5,862,799 A * | 1/1999 | Yogev et al. | 126/578 |
| 6,036,323 A * | 3/2000 | Meijer | 359/851 |
| 6,073,500 A | 6/2000 | Jorgensen et al. | |
| 6,225,551 B1 * | 5/2001 | Lewandowski et al. | 136/246 |
| 6,231,197 B1 | 5/2001 | Nakamura | |
| 6,349,718 B1 | 2/2002 | Ven et al. | |
| 6,533,452 B1 * | 3/2003 | Hardcastle, III | 374/57 |

(Continued)

*Primary Examiner*—David A. Rogers
(74) *Attorney, Agent, or Firm*—Vedder Price P.C.

(57) ABSTRACT

An accelerated weathering test apparatus including a target board operatively coupled to a reflector device. The target board is configured to support at least one test specimen for exposure to concentrated solar radiation. The reflector device is configured to reflect and concentrate solar radiation onto the at least one test specimen. The reflector device includes a bed and a plurality of mirrors. Each mirror is disposed on the bed in one of a first operative position, where solar radiation is reflected on the at least one test specimen, and a second operative position, where no solar radiation is reflected on the at least one test specimen. One of the irradiance incident on the at least one test specimen from the reflector device and the temperature of the at least one test specimen is adjustable by movement of selected mirrors from the first operative position to the second operative position in response to an input in order to control one of a temperature of the at least one test specimen or the irradiance.

50 Claims, 9 Drawing Sheets

U.S. PATENT DOCUMENTS

| | | |
|---|---|---|
| 6,597,709 B1 | 7/2003 | Diver, Jr. |
| 6,604,436 B1 * | 8/2003 | Lewandowski et al. .... 73/865.6 |
| 6,659,638 B1 * | 12/2003 | Hardcastel, III .............. 374/57 |
| 6,820,509 B2 * | 11/2004 | Lewandowski et al. .... 73/865.6 |
| 6,984,050 B2 * | 1/2006 | Nakamura ................. 359/853 |
| 2003/0121514 A1 * | 7/2003 | Davenport et al. .......... 126/570 |
| 2003/0156337 A1 | 8/2003 | Davidson et al. |
| 2004/0093965 A1 | 5/2004 | Hardcastle, III |
| 2004/0178367 A1 | 9/2004 | Fischer, Jr. et al. |
| 2004/0231716 A1 * | 11/2004 | Litwin ........................ 136/246 |

* cited by examiner

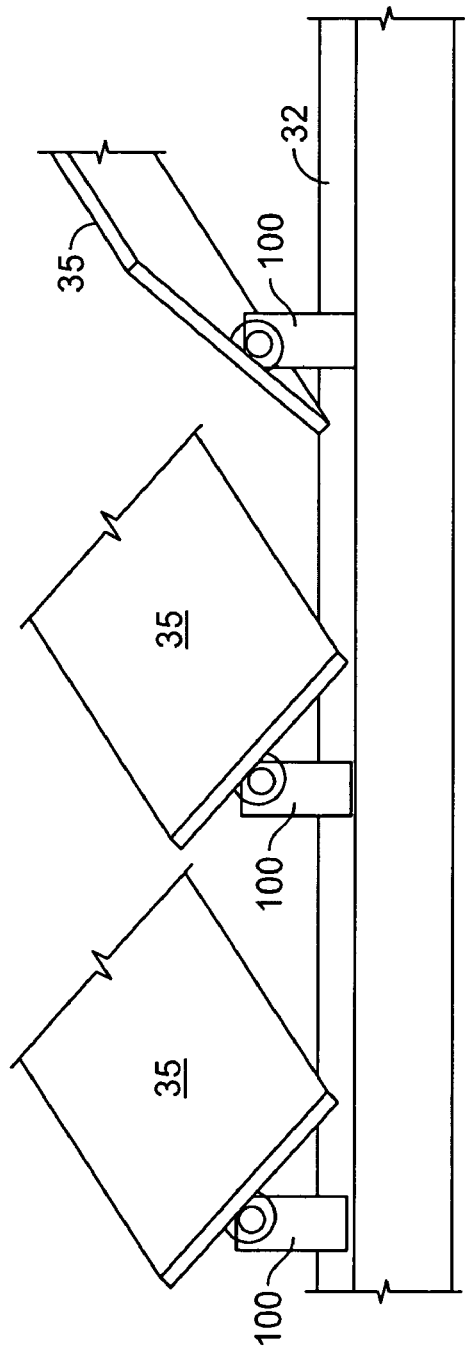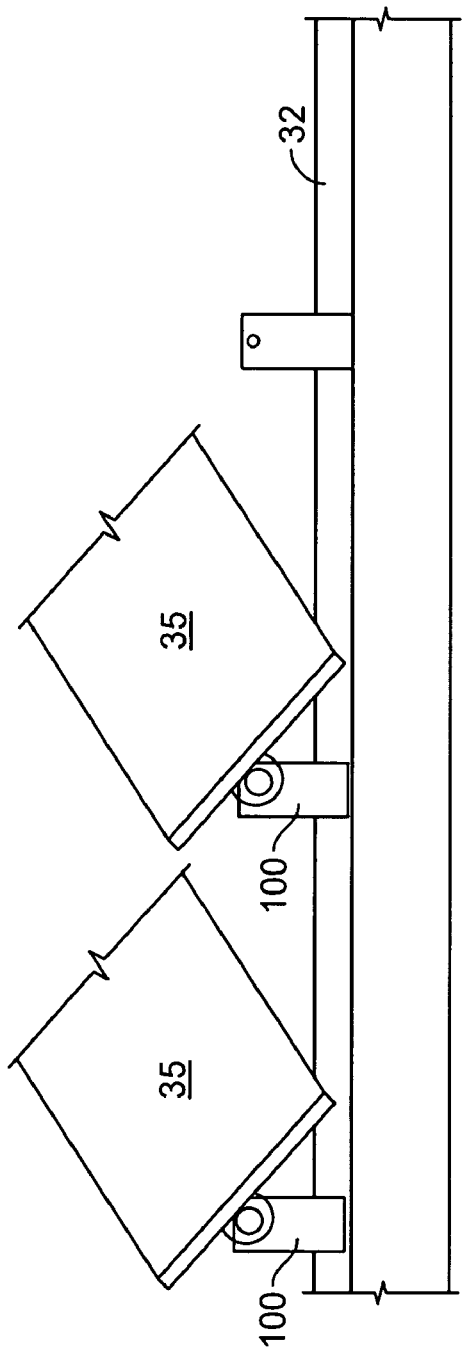

VARIABLY CONTROLLED ACCELERATED WEATHERING TEST APPARATUS

The present disclosure is directed to an accelerated weathering test apparatus of the type used to concentrate solar radiation on test specimens, and more particularly, to an accelerated weathering test apparatus where the solar radiation concentration upon on test specimens is variably controlled.

Manufacturers of exterior coatings, such as paints and finishes, as well as plastics and other components which tend to degrade under exposure to solar radiation and other weathering effects, often want to know how such products will perform following years of exposure. However, such manufacturers typically require such information in a much shorter time than it would take to expose such materials to weathering effects under normal conditions. Accordingly, accelerated weathering test devices have been developed which accelerate the effects of weathering due to outdoor exposure in a much shorter time so that manufacturers need not actually wait five or ten years in order to determine how their products will hold up after five or ten years of actual outdoor exposure.

One known accelerated weathering test device is disclosed in U.S. Pat. No. 2,945,417, issued to Caryl et al. The aforementioned test device includes a Fresnel-reflecting solar concentrator having a series of ten flat mirrors which focus natural sunlight onto a series of test specimens secured to a target board measuring approximately five (5) inches wide by fifty-five (55) inches long. The Fresnel-reflecting solar concentrator directs solar radiation onto the target board area with an intensity of approximately eight suns. Both the bed which supports the mirrors of the solar concentrator, and the target board, are supported by a frame which can be rotated to follow daily movements of the sun.

A solar tracking mechanism responsive to the position of the sun, controls the operation of an electric motor that is used to rotate the test apparatus to follow movements of the sun. The axis of rotation of the test machine is oriented in a north-south direction, with the north elevation having altitude adjustment capability to account for variation in the sun's altitude at various times during the year.

Such known testing devices are also provided with an air tunnel mounted above the target board. An air deflector causes air escaping from the air tunnel to be circulated across the test specimens mounted to the target board to prevent the test specimens from overheating due to the concentrated solar radiation to which they are exposed. The amount of air is controlled by the dimension of the gap between the deflector and the specimen. A squirrel cage blower communicates with the air tunnel for blowing cooling ambient air there through. In addition, water spray nozzles are provided proximate to target board for wetting the test samples at periodic intervals to simulate the weathering effects of humidity, dew, rain, etc.

Another known accelerated weathering test device is disclosed in U.S. Pat. No. 4,807,247 issued to Robins. The aforementioned test device includes all the structure previously described above with respect to the 417 patent and further includes a system for maintaining a uniform, constant test specimen temperature during daylight hours despite variations in ambient air temperature and variations in solar radiation intensity.

The system includes a temperature sensor mounted to the target board for exposure to the concentrated solar radiation and for generating an electrical signal indicative of the temperature of the test specimen mounted to the target board. The system further includes a control mechanism electrically coupled to the temperature sensor and responsive to the electrical signal generated thereby for selectively controlling the application of electrical power to the electrical motor included within the air circulation system. In this manner, the control mechanism serves to vary the speed of the electric motor and thereby control the flow rate of cooling ambient air circulating across the target board so that the temperature of the test specimen remains constant at the desired set point.

When the sensed temperature of the test specimen increases, the control mechanism increases the speed of the blower motor to circulate more cooling ambient air across the target board in order to lower the temperature of the test samples back to the desired set point. Similarly, if the sensed temperature of the target samples drops below the desired nominal temperature, the control mechanism decreases the speed of the blower to permit the test samples to warm up back to the desired set point.

The temperature control mechanism also includes a user operable adjustment mechanism, in the form of the control knob, for allowing a user to set a static, desired target specimen temperature. A bypass switch is also provided for allowing the user to operate the test device in the controlled temperature-mode as described above, or in an uncontrolled mode wherein the blower motor operates at a constant speed.

Standardized testing methods have been developed for operating accelerated weathering test devices of the type described above. The American Society for Testing and Materials (ASTM) has issued standards G90, E838, D4141, D3105, D3841, D5105, E1596 and D4364 covering the testing procedures and the operating parameters for conducting such outdoor accelerated weathering tests. Other standards and appraisals have also been developed and specified by the Society of Automotive Engineers (SAE), Ford, International Standards Organization (ISO), American National Standards Institute (ANSI), Japan Industrial Standard (JIS), namely, SAE J576, SAE J1961, Ford EJB-M1J14-A, Ford EST-M5P11-A, ISO 877, ANSI/NSF 54, JIS Z 2381 and MIL-T-22085D.

Apart from outdoor accelerated weathering test devices of the type described above, other test devices are also known which utilize an artificial source of radiation to expose the test specimens. An example of such a test device is disclosed in U.S. Pat. No. 3,664,188 issued to Kockott. While such test devices have the advantage of permitting precise control over radiation intensity, temperature and humidity, such test devices have often failed to duplicate the actual light spectrum of natural sunlight to which the specimens under test will actually be exposed in everyday use. It has been acknowledged and recognized by those of skill in the art that natural sunlight and artificial sunlight test apparatus are distinct from one another and provide different sets of empirical data.

Outdoor accelerated weathering test devices of the type described above in regard to U.S. Pat. Nos. 2,945,417 and 4,807,247, have the advantage of using natural sunlight, and hence the specimens under test are exposed to the actual spectrum of sunlight. However, disadvantages of outdoor accelerated weathering test devices have been discovered.

One such disadvantage is that the amount of solar radiation concentrated upon the test specimens by each flat mirror cannot be controlled because the flat mirrors may be fixedly connected to the mirror support bed. Accordingly, when the mirror support bed follows the elevation of the sun, all of the flat mirrors on the mirror bed concentrate solar radiation upon the test specimens. Therefore, as the intensity of solar radiation increases and decreases with changes of the sun, transparency of the sky, haze, fog, clouds, humidity, or barometric pressure, the temperature of the test specimen and irradiance imparted on the test specimen will accordingly change. The changes in the elevation of the sun occur daily and seasonally. On a daily basis, the intensity of solar radiation is highest each day around noon. On a seasonal basis, the intensity of solar radiation is highest during the summer. Therefore, during these high intensity periods, the temperature of the specimen may exceed beyond desired levels even with air cooling of the specimens. Additionally, without controlling the solar radiation concentrated upon the test specimens by each flat mirror, it may be difficult to maintain the temperature of the test specimens at a desired test temperature or vary the temperature of the test specimens based on a test temperature profile or cycle.

Therefore, there exists a need in the art for a device and a method of controlling the temperature, temperature fluctuations, irradiance, and irradiance fluctuations of a test specimen in an outdoor accelerated weathering test apparatus regardless of daily, seasonal, and other variations in the intensity of solar radiation.

BRIEF DESCRIPTION OF THE DRAWINGS

Certain embodiments are shown in the drawings. However, it is understood that the present disclosure is not limited to the arrangements and instrumentality shown in the attached drawings, wherein:

FIG. 10 illustrates a perspective view of one embodiment of a method of controlling a reflective surface for a weathering test apparatus constructed in accordance with the teachings of the present disclosure; and FIG. 11 illustrates a perspective view of another embodiment of a method of controlling a reflective surface for a weathering test apparatus constructed in accordance with the teachings of the present disclosure.

DETAILED DESCRIPTION

Figure 1:
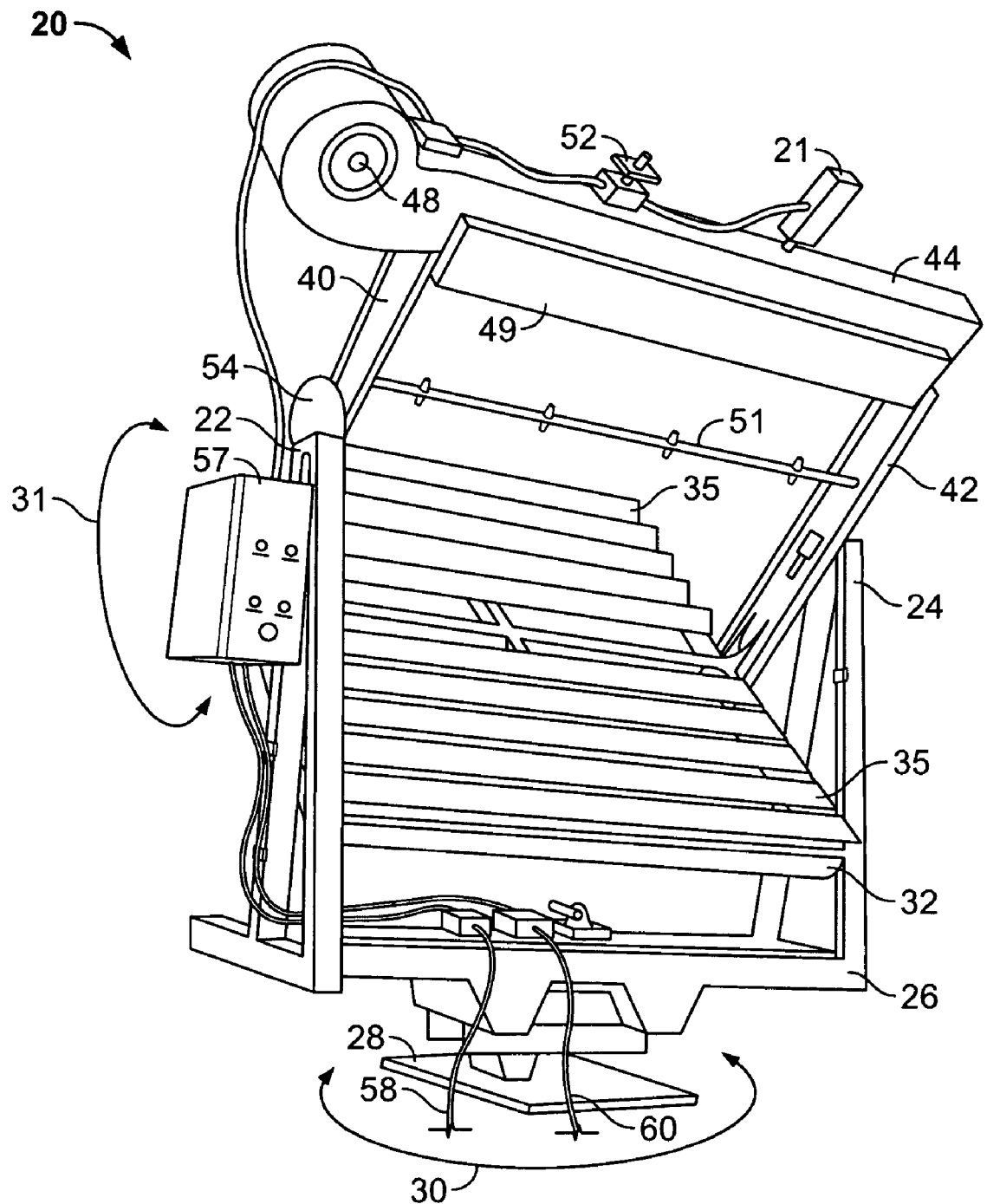
FIG. 1 illustrates a perspective view of a prior art weathering test apparatus.

For the purposes of promoting and understanding the principles disclosed herein, reference will now be made to the preferred embodiments illustrated in the drawings and specific language will be used to describe the same. It will nevertheless be understood that no limitation of the scope is thereby intended. Such alterations and further modifications in the illustrated device and such further applications are the principles disclosed as illustrated therein as being contemplated as would normally occur to one skilled in the art to which this disclosure relates.

In accordance with one principle aspect to the present disclosure, an accelerated weathering test apparatus includes a target board operatively coupled to a reflector device. The target board is configured to support at least one test specimen for exposure to concentrated solar radiation. The reflector device is configured to reflect and concentrate solar radiation onto the at least one test specimen. The reflector device includes a bed and a plurality of mirrors. Each mirror is disposed on the bed in one of a first operative position, where solar radiation is reflected on the at least one test specimen, and a second operative position, where no solar radiation is reflected on the at least one test specimen. One of the irradiance incident on the at least one test specimen and the temperature of the at least one test specimen is adjustable by movement of selected mirrors from the first operative position to the second operative position in response to an input in order to control one of a temperature level and irradiance level of the at least one test specimen.

In accordance with another principle aspect of the present disclosure, a method for adjusting one of an irradiance incident on at least one test specimen and a temperature of the at least one test specimen in an accelerated weathering test apparatus includes the following steps: (a) fitting the apparatus with a target board operatively coupled to a reflector device, where the target board is configured to support the at least one test specimen, the reflector device is configured to reflect and concentrate solar radiation on to the at least one test specimen and the reflector device includes a bed with a plurality of mirrors; (b) operatively coupling each mirror to the bed such that each mirror is independently disposed on the bed in one of a first operative position, where solar radiation is reflected on the at least one test specimen, and a second operative position, where no solar radiation is reflected on the at least one test specimen; and (c) controlling a plurality of devices, where each device is operatively coupled to one mirror, with a controller to selectively activate the devices to facilitate movement of the mirrors from the first operative position to the second operative position in response to an input.

For the purposes of promoting and understanding the principles disclosed herein, reference will now be made to the preferred embodiments illustrated in the drawings and specific language will be used to describe the same. It will nevertheless be understood that no limitation of the scope is thereby intended. Such alterations and further modifications in the illustrated device and such further applications are the principles disclosed as illustrated therein as being contemplated as would normally occur to one skilled in the art to which this disclosure relates.

Referring to FIG. 1, a prior art accelerated weathering test apparatus is designated generally by reference 20 and includes a pair of A-frame members 22 and 24 to support the operative portion of the apparatus. The lower ends of the A-frame members 22, 24 are interconnected by a base member 26 which is operatively connected to a ground member 28 in order to provide azimuth rotation in the direction indicated by arrow 30 and elevation rotation in the direction indicated by arrow 31. The elevation direction rotation accounts for periodic variation in the sun's altitude throughout the day.

Rotatively supported from the upper ends of A-frame members 22, 24 is a mirror bed frame 32 which supports a plurality of flat mirrors 35. A pair of standards 40 and 42 extend outwardly from and perpendicular to mirror bed frame 32. The plurality of mirrors 35 are angled to reflect solar radiation directly impinging upon such mirrors to a target board 38 (see FIG. 2). In FIG. 1, the mirror bed frame 32 is shown as having ten mirrors 35. The mirror bed frame 32 is symmetric about the pair of standards 40 and 42. Accordingly, five mirrors 35 are positioned on each side of the standards 40 and 42, with each mirror 35 having a symmetric counterpart on the other side of the standards 40 and 42. Therefore, in the following, any reference to a mirror 35 on one side of the standards 40 and 42 also refers to the counterpart mirror 35 on the other side of the standards 40 and 42.

Figure 3:
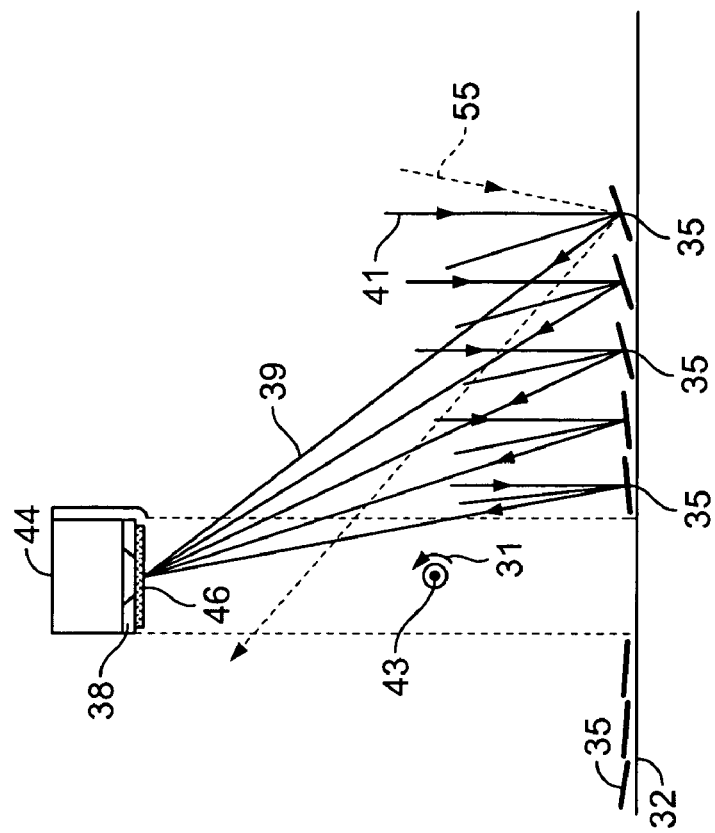
FIG. 3 illustrates a schematic diagram of an aspect of the operation of the weathering test apparatus of FIG. 1.
Figure 2:
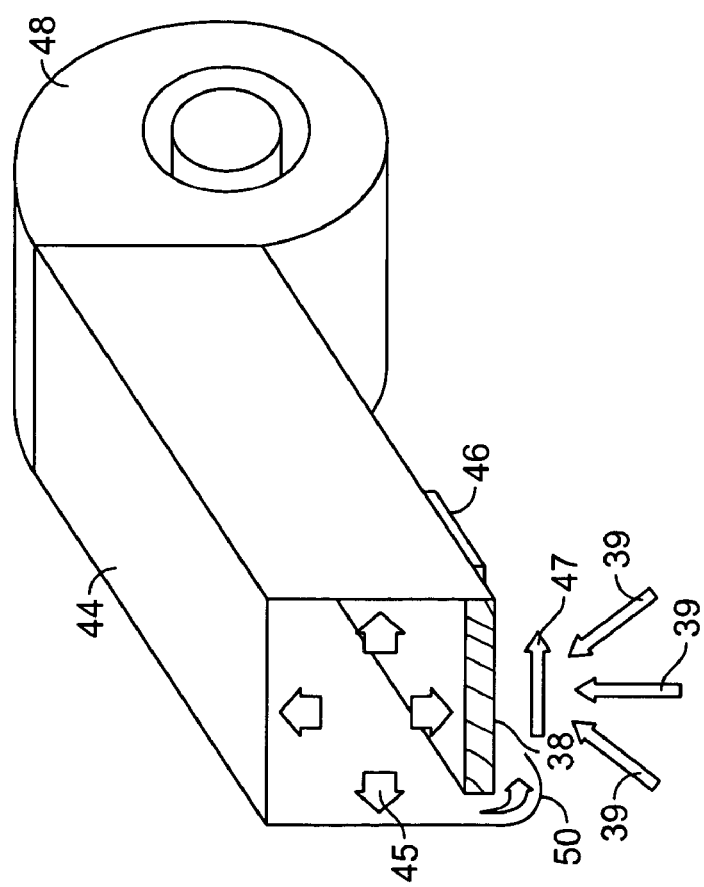
FIG. 2 illustrates a perspective view of a blower assembly of the weathering test apparatus of FIG. 1.

An air tunnel 44 having a generally rectangular cross section is supported by the upper ends of standards 40, 42. Referring to FIGS. 2 and 3, target board 38 is supported by the lower wall of air tunnel 44, and a plurality of test specimens 46 are mounted to the target board 38 for exposure to the concentrated solar radiation, represented in FIG. 2 by the upwardly extending arrows numbered 39. The target board 38 may include a single specimen 46 or a plurality of similar or different specimens 46. A squirrel cage blower assembly 48 communicates with one end of the air tunnel 44. Squirrel cage blower assembly 48 includes a fan driven by an electric motor to circulate cooling ambient air through air tunnel 44, represented in FIG. 2 by the outwardly extending arrows numbered 45. As shown in FIG. 2, air tunnel 44 includes a deflector 50 which extends for the length of target board 38 and causes cooling ambient air to be circulated across target board 38 for cooling test specimens 46, represented in FIG. 2 by the arrows numbered 47.

Standards 40, 42 are rotatively supported to upper ends of A-frame members 22, 24. A supporting shaft 43 (shown in FIG. 3) coincident with the axis of rotation in passing through standards 40, 42 rotably supports that portion of the test apparatus which tracks daily movements of the sun. In order to properly position the mirror bed frame 32, a reversible electric motor and related gear drive, which are generally designated by reference number 54, are provided for periodically rotating the mirror bed frame 32 and target board assembly to track the movements of the sun. A clutch (not shown) preferably couples standard 40 to the shaft 43 to rotate the mirror bed frame 32 and target board assembly while permitting manual positioning of the unit at any time to correct for any positioning errors.

A Solar cell tracking unit 52 controls the application of electrical power to a reversible motor in order to maintain the mirror bed frame 32 perpendicular to incident rays of sunlight. The Solar cell tracking unit 52 may be of the type which includes two balanced photo cells (not shown) and a shadowing device (not shown) mounted above such photo cells for shading them. When an imbalance is detected resulting from one photo cell receiving more sunlight than the other photo cell, an electrical error signal is generated which is amplified and used to apply power to the drive motor 54 for rotating the unit until the photo cells are again balanced, indicating that the unit is properly positioned with respect to the sun.

Also shown in FIG. 1 is a water spray nozzle assembly, designated generally by reference numeral 51. As shown in FIG. 1, spray nozzle assembly 51 is used to periodically spray water at the test specimens to simulate dew, rain, etc.

A hinge shield or cover 49 is shown coupled to the air tunnel 44 opposite the air deflector 50. A door release mechanism 21 is disposed on the air tunnel 44 for engaging and maintaining the shield in an open position. Upon release, the shield 49 assumes the closed position such that concentrated solar radiation reflected by the plurality of mirrors 35 does not reach the test specimens 46.

Secured to the target board 38 is a feedback device (not shown) having at least one temperature sensitive component secured in heat conductive relationship therewith. Such component may be a thermistor, thermocouple, resistance temperature device, integrated circuit temperature device or any other suitable device for detecting temperature of the feedback device. The feedback device may be formed from a standardized material having known thermal conductive properties or may be formed from a material similar to that of the test specimen. The temperature sensitive component may be embedded within, attached to a back surface or attached to a front surface of the feedback device. Alternatively, a non-contact optical temperature sensing device may be used in order to determine the temperature of the feedback device. The feedback device is preferably coated with black paint to insure that the feedback device will absorb solar radiation impinging upon the area of the target board 38 to which the feedback device is secured. An appropriate black paint which may be used for this purpose is DUPONT DULUX Super Black High Temperature Enamel.

The temperature sensitive component of the feedback device or the above-described sensing of the feed back device's temperature may represent the temperature of the specimen 46. Alternatively, the apparatus 20 can include one or more contact or non-contact temperature sensors (not shown) near or on the test specimen that can provide signals indicative of the temperature of the test specimen. In the following, any reference to a temperature sensor can represent a device that measures the temperature of the feedback device, as described above, or a device that directly measures the temperature of the test specimen. The apparatus 20 may also receive irradiance data from one or more irradiance sensors (not shown) that can be disposed on the apparatus 20 or remotely relative to the apparatus 20.

Referring again to FIG. 1, a controller box 57 houses the power and controller systems for the apparatus 20. A power cable 58 supplies electrical power to the apparatus 20 for powering electric motor, which actuates the fan 48. A signal cable 60 is connected to the controller system disposed within the control box 57 for communication with remotely disposed devices, such as the feedback devices and input device, as will be discussed below or for communication with a central command for governing the operation of the apparatus 20 in accordance with the present invention.

Referring to FIG. 3, an aspect of operation of the weathering test device 20 is schematically shown. Each mirror 35 has a fixed angle relative to the mirror bed 32. The angle of each mirror 35 is adjusted so that upon the incident solar rays 41 striking each mirror 35, reflected solar rays 39 are directed toward the test specimen 46. When the elevation of the sun changes in the sky, the entire mirror bed 32 can be rotated about the shaft 43 as shown by the arrow 31 to ensure that the reflected solar rays 39 strike the test specimen 46. Accordingly, in the weathering test device 20 of FIGS. 1, 2 and 3, the position of the mirrors 35 relative to the mirror bed 32 is fixed. Therefore, if the mirror bed 32 is adjusted according to the azimuth and elevation of sun, the test specimen 46 will receive reflected solar rays 39 from all of the mirrors 35.

Figure 4:
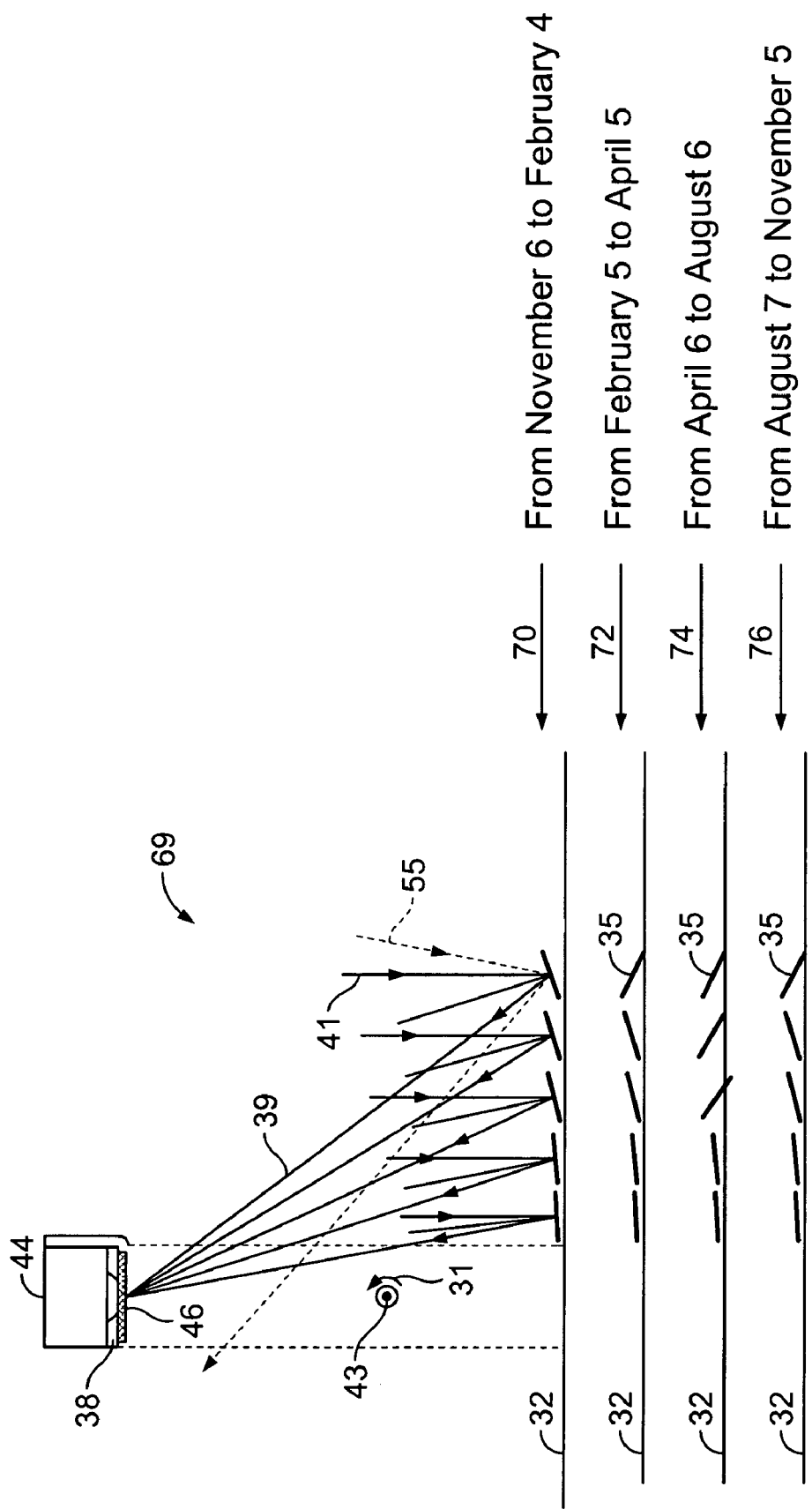
FIG. 4 illustrates a schematic diagram of one aspect of the operation of a weathering test apparatus constructed in accordance with the teachings of the present disclosure.

Referring to FIG. 4 a schematic diagram of a temperature/irradiance adjustment fixture 69 constructed in accordance with one embodiment of the present disclosure is shown. In the temperature/irradiance adjustment fixture 69, the operation of each mirror 35 can be controlled to place each mirror 35 between an operative position and an inoperative position.

In the operative position, a mirror 35 fully directs reflected solar rays 39 toward the test specimen 46. In the inoperative position, however, a mirror 35 does not direct any reflected solar rays 39 toward the test specimen 46. As will become apparent from the following, in a first embodiment of the present disclosure, the angle of each mirror 35 can be adjusted to position the mirror 35 at the operative position or the inoperative position. In a second embodiment of the present disclosure, the surface of each mirror 35 can be fully covered to place the mirror 35 in the inoperative position. In a third embodiment of the present disclosure, each mirror 35 can 15. be entirely removed from the mirror bed 32 to place that mirror 35 in the inoperative position.

Referring to FIG. 4, four operational configurations of the temperature/irradiance adjustment fixture 69 in accordance with the first embodiment are shown. The four operational configurations represent four seasonal configurations. The seasons may generally correspond to winter, spring, summer and fall. The first seasonal configuration, which corresponds to winter, is shown by reference numeral 70 (generally from December 6 to February 4 in the northern hemisphere). During the winter season, the elevation of the sun is typically at its lowest compared to the other seasons. During weathering tests, it may be desired or necessary to maintain the temperature/irradiance of the test specimen 46 at a constant temperature/irradiance or following a particular temperature/irradiance profile. For brevity, this desired constant temperature/irradiance or temperature/irradiance profile will be referred to herein as the desired temperature/irradiance. Accordingly, to maintain the temperature/irradiance of the test specimen 46 at the desired temperature/irradiance, all of the mirrors 35 may be needed to direct the reflected solar rays 39 toward test specimen 46 to keep the test specimen 46 at the desired temperature/irradiance. During the winter season, all the mirrors 35 may be needed because the intensity of the incident solar rays 41 is low due to the lower elevation of the sun in the sky.

The second seasonal configuration, which corresponds to spring, is shown by reference numeral 72 (generally from February 5 to April 5 in the northern hemisphere). During the spring season, four of the five mirrors 35 are shown to be in the operative position, while one mirror 35 is placed in the inoperative position. During the spring season, the elevation of the sun is generally higher in the sky than the winter season. Accordingly, to maintain the temperature/irradiance of the test specimen 46 at the desired temperature/irradiance, all of the mirrors 35 may not be needed to direct the reflected solar rays 39 toward the test specimen 46.

During the summer season, as shown by reference numeral 74 (generally from April 6 to August 6 in the northern hemisphere), the elevation of the sun may be at its highest. Accordingly to maintain the test specimen 46 at the desired temperature/irradiance, only a few of the mirrors 35 may be needed. As shown in the summer configuration 74, only two mirrors 35 of the five may be necessary to direct the reflected solar rays 39 toward the test specimen 46 to maintain the temperature/irradiance of the test specimen 46 at the desired temperature/irradiance.

The last seasonal configuration 76 of FIG. 4 represents the fall season (from August 7 to November 5 in the northern hemisphere), where the elevation of the sun may be very similar to the spring season as represented by configuration 72. Accordingly, only three of the mirrors 35 may be needed to maintain the temperature/irradiance of the test specimen 46 at the desired temperature/irradiance. As shown in configuration 76, two of the mirrors 35 are placed in the inoperative position.

Using a fewer number of mirrors 35 that are necessary for maintaining the desired temperature/irradiance may lower the temperature/irradiance of the test specimen 46 below the desired temperature/irradiance. In contrast, using a larger number of mirrors 35 that are necessary for maintaining the desired temperature/irradiance may raise the temperature/irradiance of the test specimen 46 above the desired temperature/irradiance. Therefore, the number of mirrors 35 that are placed in the first operative position directly affect the temperature/irradiance of the test specimen 46. With the temperature/irradiance fixture 69, the temperature/irradiance of the test specimen 46 can be substantially maintained near the desired temperature/ irradiance all year around by placing only the necessary number of the mirrors 35 in the operative position.

Figure 5:
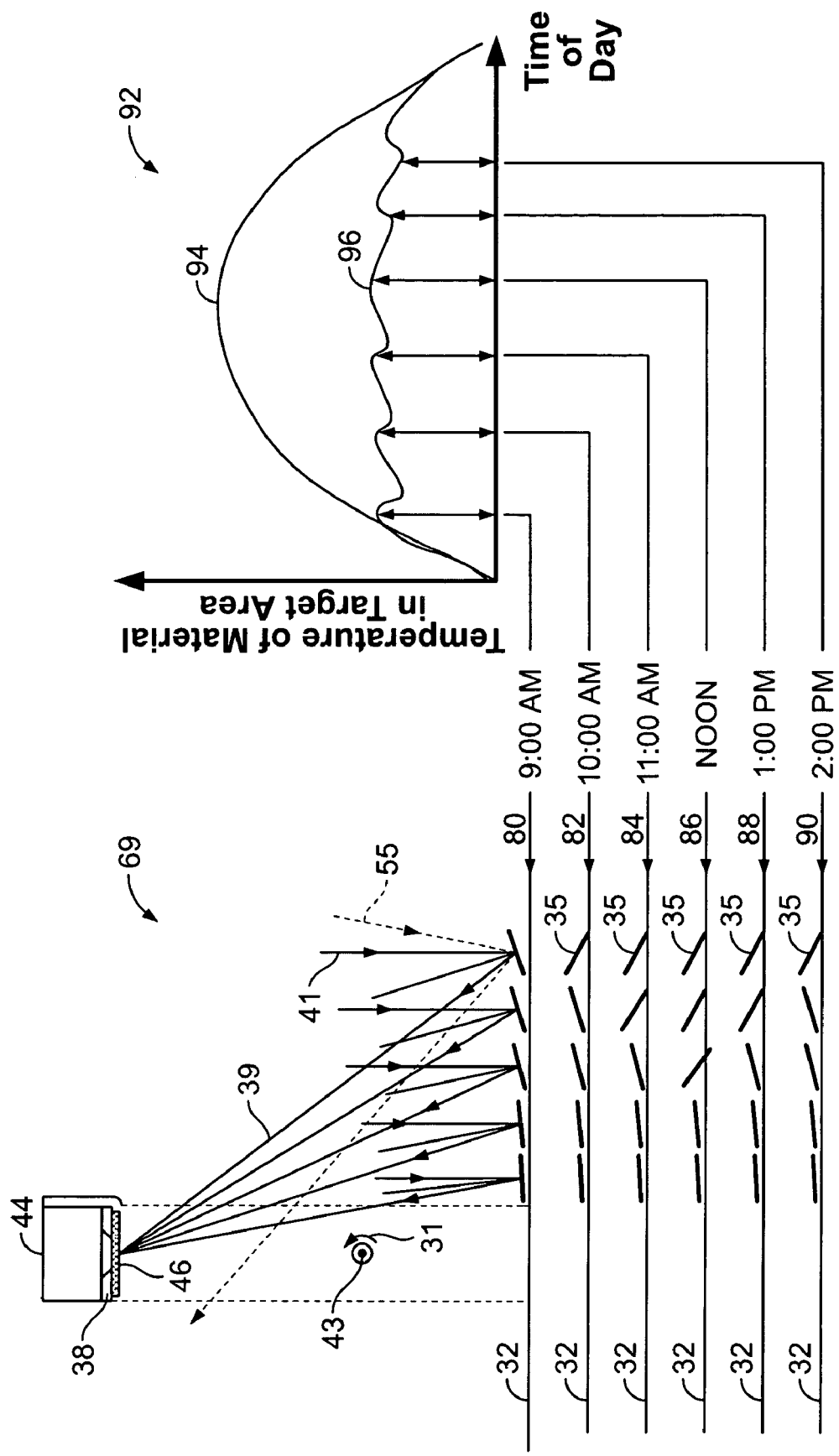
FIG. 5 illustrates a schematic diagram of another aspect of the operation of a weathering test apparatus constructed in accordance with the teachings of the present disclosure.

The temperature/irradiance adjustment fixture 69 can maintain the temperature/irradiance of each test specimen 46 at the desired temperature/irradiance during each day when the elevation of the sun varies between the morning elevation and the evening elevation. Referring to FIG. 5, six daily operational configurations for the mirrors 35 are shown by reference numbers 80 through 90. At the first daily configuration 80, which generally corresponds to 9:00 a.m., the elevation of the sun is relatively low in the sky. Accordingly, all of the mirrors 35 may be needed to direct the reflected solar rays 39 toward the test specimen 46 to maintain the test specimen 46 at the desired temperature/irradiance. At 10:00 a.m., when the elevation of the sun is slightly higher in the sky than 9:00 a.m., the temperature/irradiance of the test specimen 46 may be maintainable near the desired temperature/irradiance with less than five operative mirrors 35. As shown by the exemplary configuration 82, four of the mirrors 35 are used to maintain test specimen 46 at the predetermined temperature/irradiance at 10:00 a.m. As the elevation of the sun increases in the sky, the intensity of the reflected solar rays 39 also increases. Accordingly as the time approaches the time when the intensity of the reflected solar rays 39 is at its highest, which may be around noon, a large number of the mirrors 35 may be placed in the inoperative position to maintain the temperature/irradiance of the test specimen 46 at the desired temperature/irradiance. As shown by configuration 86, which generally corresponds to noon, only two of the mirrors 35 are used to maintain the test specimen 46 at the desired temperature/irradiance. As the elevation of the sun progressively lowers during the afternoon and toward the evening hours, a larger number of the mirrors 35 may again be needed to maintain the test specimen 46 at the desired temperature/irradiance. As shown by configuration 88, at 1:00 p.m. three of the mirrors 35 may be needed to maintain the test specimen 46 at the desired temperature/irradiance. As shown by the configuration 90, at 2:00 p.m., four mirrors 35 may be needed to maintain the test specimen 46 at the desired temperature/irradiance.

Referring to the right side of FIG. 5, a graph 92 representing temperature of the test specimen 46 versus the time of day is shown for the configurations 80-90 of FIG. 4. The graph 92 shows two sets of data plotted as a first curve 94 and a second curve 96. The first curve 94 corresponds to a weathering test apparatus 20, such as the one shown in FIGS. 1 to 3, where the mirrors 35 are either fixed to the mirror bed frame 32 or the amount of light reflected from the mirrors 35 toward the test specimen 46 is in no way adjustable. As shown by the first curve 94, the temperature of the test specimen 46 does not remain constant. As the day progresses, the temperature of the test specimen 46 increases with the rising elevation of the sun. The temperature of the test specimen 46 may peak at around noon. The temperature of the test specimen 46 then progressively lowers with the lowering of the sun in the afternoon. Accordingly, the temperature of the test specimen 46 cannot be maintained at or near a desired temperature.

Referring now to the second curve 96, an exemplary result of the disclosed temperature/irradiance adjustment fixture 69 is graphically shown by the second curve 96. Because the intensity of the reflected solar rays 39 striking the test specimen 46 is controlled throughout the day by one or more mirrors 35 being placed between the operative position and the inoperative position, the temperature of the test specimen throughout the day can be maintained near a desired temperature. As shown by the second curve 96, small oscillations in the temperature of the test specimen 46 may occur during the day between each operational configuration. These small oscillations may be partly due the time increment at which the mirrors are configured between the operative and inoperative positions. Additionally, the small oscillations may be partly due to the number of mirrors 35 that are on the mirror bed 32. Accordingly, to reduce the oscillations, the number of mirrors 35 may have to be increased.

Figure 6:
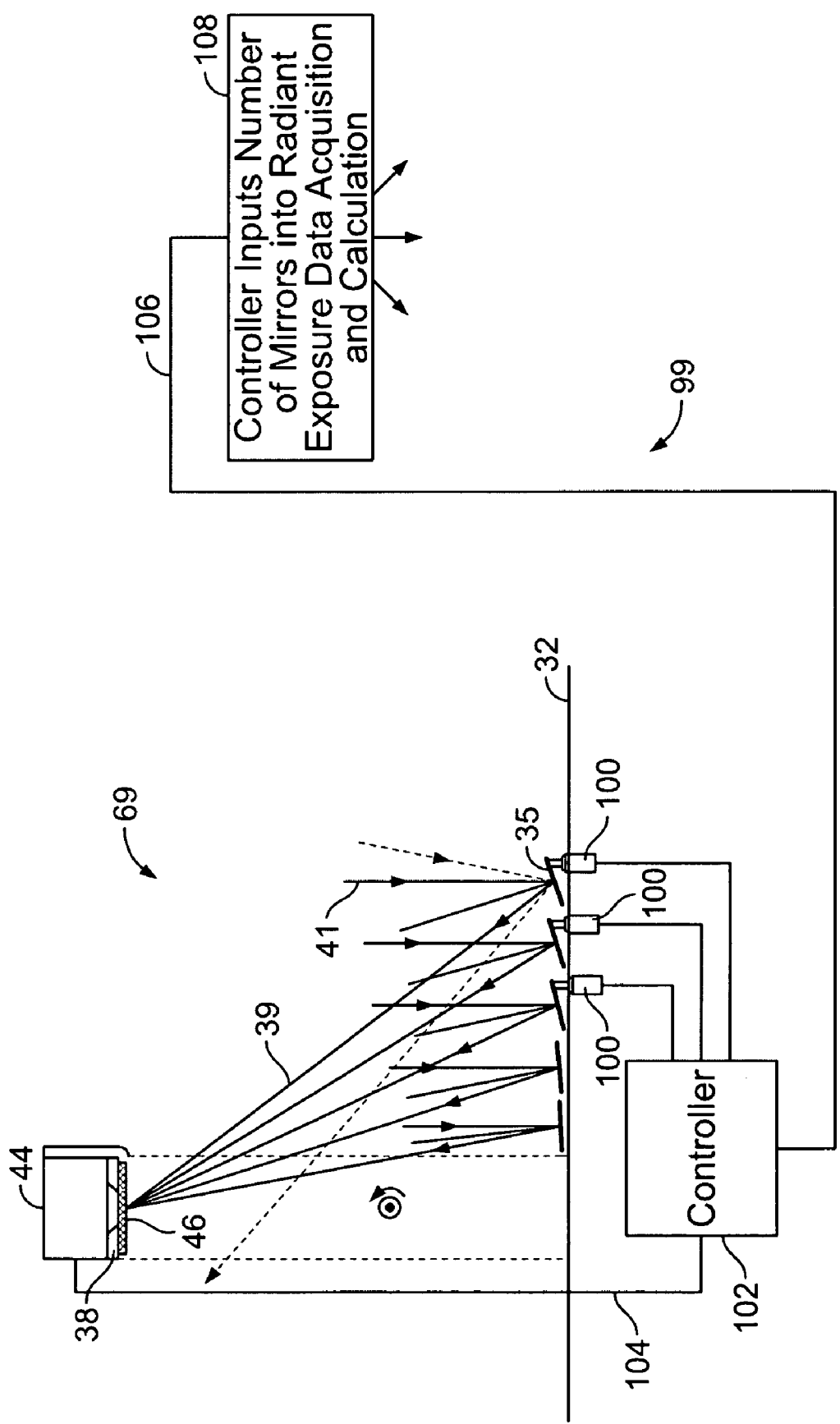
FIG. 6 illustrates a schematic diagram of one embodiment of a control system of a weathering test apparatus constructed in accordance with the teachings of the present disclosure.

Referring to FIG. 6, a control system 99 for the disclosed temperature/irradiance adjustment fixture 69 is schematically shown. Each mirror 35 is operatively coupled to a device that can move the mirror 35 between the operative position and the inoperative position. In FIG. 6, each device is shown to be an actuator 100. Each actuator 100 is connected to a controller 102 to receive control signals. The controller 102 receives temperature and solar irradiance data 104 from the temperature sensor(s) and local or remote irradiance sensor(s). The controller 102 communicates by a wired or wireless link 106 with a data acquisition and calculations system 108, which may be referred to herein as the computing system 108. The controller 102 provides the computing system 108 with data regarding the number of mirrors 35, the temperature of the test specimen 46 and solar irradiance data 104. Based on the irradiance data 104, the controller 102 may then perform calculations to determine which mirrors 35 at what time should be at any one of the operative position or the inoperative position. The computing system 108 provides data logging for the apparatus 20. The data logging may include, for example, specimen exposure and response to such exposure during hourly, daily, or weekly testing cycles.

With reference to FIG. 4, the controller 102 may, for example, change the configurations of the mirrors 35 from the configuration 70 to configuration 72 based on the date changing from February 4 to February 5. Additionally, based on the data received from the temperature/irradiance sensors, the controller 102 may change the configuration of the mirrors 35 to a different configuration than those shown in FIG. 4 due to possibly unusual warm days during the winter, for example, or unusually cool days during the summer. Accordingly, the controller 102 can configure the mirrors 35 to compensate for variable environmental factors to control the temperature of the specimen 46 and the irradiance imparted on the specimens 46. Such factors may include haze, clouds, fog and/or barometric pressure.

Figure 7:
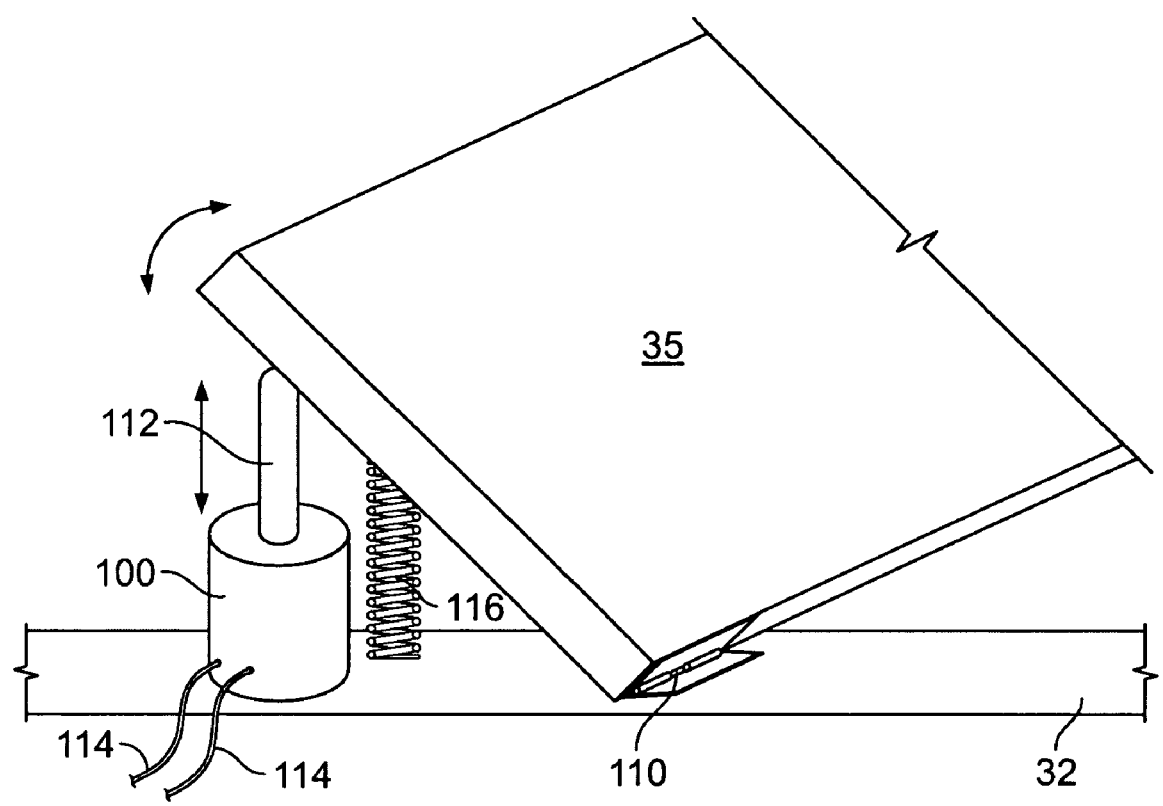
FIG. 7 illustrates a perspective view of one embodiment of an actuation device of a reflective surface for a weathering test apparatus constructed in accordance with the teachings of the present disclosure.

Referring to FIG. 7, one embodiment of the disclosed temperature/irradiance adjustment fixture 69 is shown where each mirror 35 is moved or can be moved between the operative position and the inoperative position. Associated with each mirror 35 is an actuator 100 that includes an actuator arm 112. The actuator arm 112 is coupled to the mirror 35 such that movement of the actuator arm 112 pivots the mirror 35 about a hinge 110. The actuator 100 receives power from power cords 114. The actuator 100 can be any type of device that provides rotational or transitional motion. For example, the actuator 100 can be a solenoid, a linear actuator, a motor, a stepper motor, a pneumatic actuator, a hydraulic actuator, or a bi-metallic actuator. When the actuator 100 is powered, the actuator arm 112 moves upward to pivot the mirror 35 about the hinge 110 to change the angle of the mirror 35. The power cord 114 may also include actuation signals from the controller 102 in order to control the movement of the actuator arm 112. Accordingly, the controller 102 can control the upward or downward travel of the actuator arm so that a desired angle for the mirror 35 is achieved. When the actuator 100 is turned off, the spring 116, which couples the mirror 35 to the mirror bed frame 32, biases the mirror 35 back to a position where the mirror 35 is inoperative.

Figure 8A:
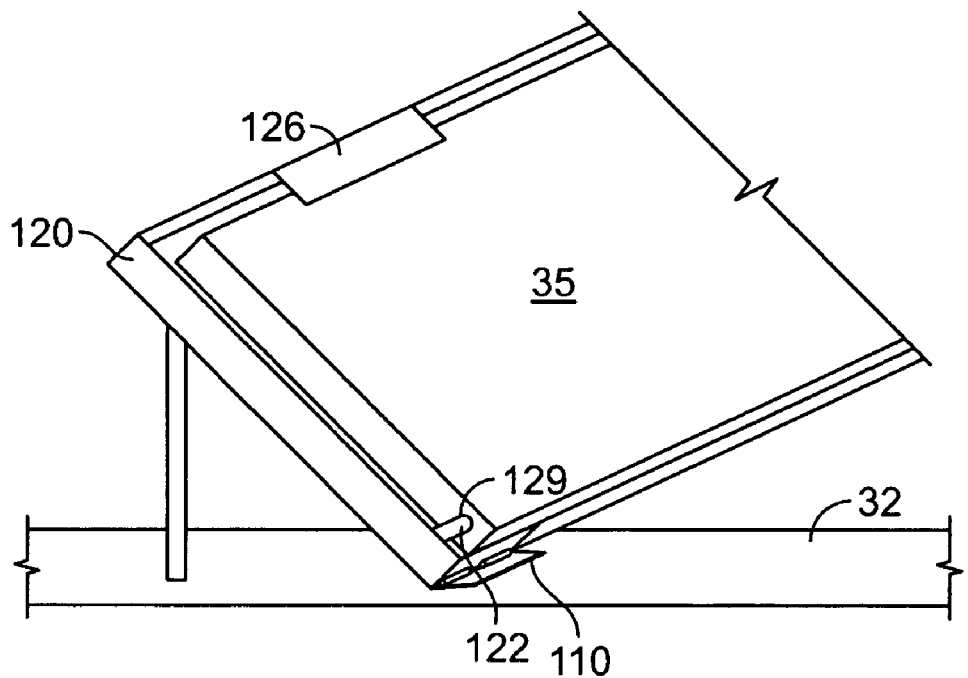
FIGS. 8A and 8B illustrate perspective views of another embodiment of an actuation device of a reflective surface for a weathering test apparatus constructed in accordance with the teachings of the present disclosure shown in the actuated and non-actuated configurations, respectively.
Figure 8B:
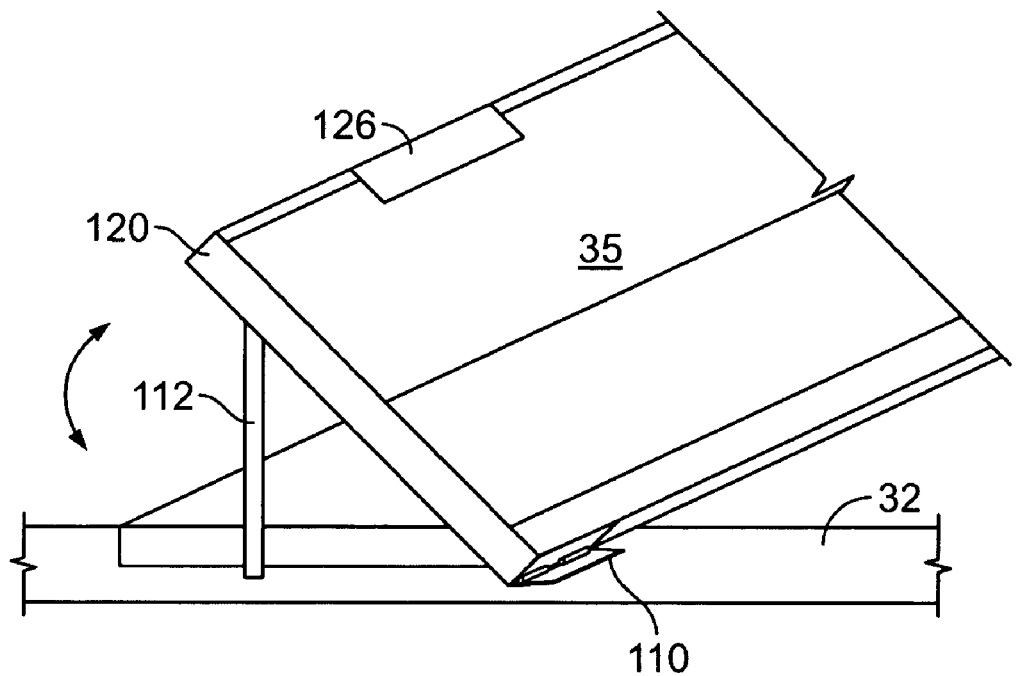

As shown in FIGS. 8A and 8B, in another embodiment of the disclosed temperature/irradiance adjustment fixture 69, each mirror 35 may include a frame 120 that is fixedly positioned relative to the mirror bed 32. The mirror 35 is coupled to the actuator arm 112, by which the mirror can be adjusted to any angle desired up to the maximum dictated by the angle of the frame 120. However, a stop tab 126 disposed on the frame 120 prevents the mirror from being positioned at an angle that is higher than the fixed angle of the frame 120. Accordingly, the angle of the mirror 35 can never exceed a maximum angle that it set by the angle of the frame 120. The mirror 35 pivots relative to the frame 120 about a pivot pin 122. The pivot pin 122 is coupled to the mirror 35 through an aperture 124 in the mirror 35. The mirror 35 is also pivotally coupled to the mirror bed 32 with the hinge 110 (as shown in FIGS. 8A and 8B).

Figure 9:
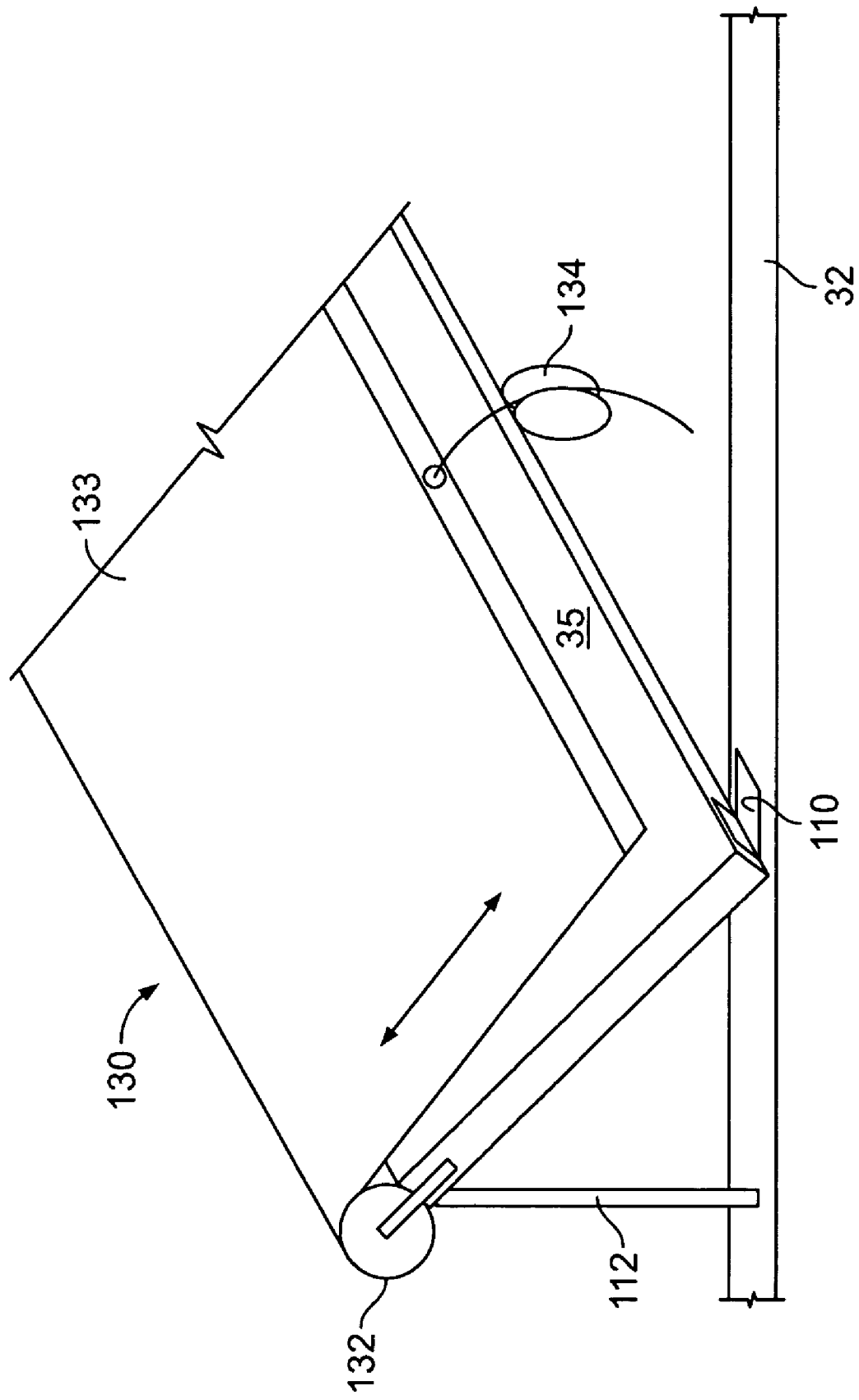
FIG. 9 illustrates a perspective view of one embodiment of a light control apparatus of a reflective surface for a weathering test apparatus constructed in accordance with the teachings of the present disclosure.

Referring to FIG. 9, as shown in another embodiment of the disclosed temperature/irradiance adjustment fixture 69, to provide more control as to how much light each mirror 35 can reflect toward the test specimen 46, each mirror 35 can also include a roller shade 130 to partially or fully block the mirror 35 if desired. To fully block the mirror 35, the shade 130 can be constructed from fully light blocking material. To partially block the mirror 35, the shade 130 can be opaque or partially transmittant, such as a neutral density filter or screen. Other materials may also be used to selectively filter different wavelengths of the solar spectrum, such as controlling the infra-red radiation to control the temperature of the test specimens 46

The mirror 35 that is shown in FIG. 9 is in many ways similar to the mirror 35 shown in FIG. 7, however, the mirror 35 in FIG. 9 also includes a roller shade 130 attached thereto. Roller shade 130 includes a roller assembly 132 that can be attached to any side of the mirror 35. In FIG. 9, the roller assembly 132 is attached to the top of the mirror 35. Roller shade 130 operates in many ways similar to the roller shades are commonly used in households to block sunlight from coming into a room. The roller shade 130 includes the roller assembly 132, a shade 133, and a cord 134 that is connected to the edge of the shade 133. By pulling on the cord 134, the shade 133 can be unwound from the roller assembly 132 to cover the mirror 35. Although not shown in FIG. 9, the cord 134 can be coupled to a motor (not shown). Accordingly, operation of the roller shade 130 may be coordinated with the operation of the motor through the controller 102. Therefore, the controller 102 may deploy the roller shade 130 at anytime that may be necessary. Alternatively, the cord 134 can be pulled manually to cover a mirror 35.

Although not shown, the mirrors 35 can be fixedly attached to the mirror bed 32 and include the roller shades 130. Accordingly, the operative position of the mirror 35 may be defined as a position where the roller shade 130 is fully retracted. The inoperative position of the mirror can be defined as a position where the roller shade 130 is unwound from the roller 132 to cover the entire surface of the mirror 35 to provide full blockage of the mirror 35. Accordingly, instead of changing the angle of the mirror 35 to move the mirror between the operative position and the inoperative position, the mirror 35 can be fully exposed, or be fully blocked.

Referring to FIGS. 10 and 11 two operational scenarios are shown where a mirror 35 can be either moved between the operative position and a inoperative position, or can be completely removed from the mirror bed 32 (shown). Referring back to FIG. 5, if the angles of the mirrors 35 are adjusted on a daily basis, each of the mirrors 35 can be positioned at the operative position and the inoperative position. As shown in FIG. 10, one of the three mirrors 35 is placed in the inoperative position. Depending upon the time of the day, however, that mirror 35 may be moved to the operative position within an hour or less to provide the necessary reflected solar rays 39 to maintain the temperature/irradiance of the test specimen 46 at the desired temperature/irradiance. Accordingly, the mirror 35 may be moved continuously between the operative position and the inoperative position throughout the day or based on some time increment.

Referring to FIG. 11, one mirror 35 is shown to have been removed from the mirror bed frame 32. The configuration of the mirror bed frame 32 as shown in FIG. 11 may be desirable when the temperature/irradiance adjustment fixture 69 is used to keep the temperature/irradiance of the test specimen 46 at the desired temperature/irradiance based on seasonal variations. For instance, and with reference back to FIG. 4, during a three-month span of time that generally represents one of the seasons shown in FIG. 4, one of the mirrors 35 on the mirror bed 32 may not be needed at all. Accordingly, that mirror 35 can be removed from the mirror bed frame 32 during that season. Removal of the mirror 35 reduces the exposure of that mirror 35 to the elements, and thereby, reduces the wear and corrosion of that mirror 35. Additionally, by removing one or more mirrors 35 from the mirror bed frame 32, the controller 102 and the computing system 108 have a smaller number of mirrors 35 to control and receive data from, respectively. Accordingly, the resources of the controller 102 and the computing system 108 can be used to perform additional functions, data acquisitions, or data processing with respect to the mirrors 35 that are operational on the mirror bed frame 32.

Although several embodiments of the present temperature disclosure fixture are disclosed above, one of ordinary skill in the art will readily appreciate that any single one of these embodiments or a combination of any one of these embodiments can be used to control the temperature/irradiance of the test specimen 46. For example, as shown in FIG. 9, each mirror 35 can be placed between the operative and inoperative positions with the actuator 110 in addition to having the roller shade 130 covering the surface of the mirror 35. As described above, only the roller shade 130 may be used as a temperature/irradiance adjustment mechanism. Alternatively, as shown in FIGS. 7, 8A and 8B, only the angular variation of each mirror 35 may be utilized to control the reflected solar rays 41 that are directed toward the test specimen 46. Alternatively yet, regardless of whether each mirror 35 has the actuation mechanism in FIGS. 7, 8A and 8B, and/or the roller shade mechanism shown in FIG. 9, each mirror 35 can be removed from the mirror bed 32, as illustrated in FIG. 11, to provide additional control for the temperature/irradiance adjustment fixture 69 of the present disclosure. It will be recognized by one of ordinary skill in the art that the first operable position and second operable position as fully described and enabled herein may also be described, enabled and associated with a first state and a second state directed to a movement of the mirrors, a removal of the mirrors, or a covering of the mirrors, and freely substitutable therefor.

As shown in FIGS. 4 and 5 and described in the foregoing, the mirrors 35 can be adjusted at different time increments or seasonal increments to maintain the test specimen 46 at a desired temperature/irradiance or subject the test specimen 46 to various temperature/irradiance cycles. For example, the configurations of the mirrors 35 can be changed every half hour, every two hours, everyday or at anytime increment desired to achieve desired results for the temperature/irradiance of the test specimen 46. The mirrors 35 can be adjusted to subject the test specimen 46 to various temperature/irradiance cycles during the test period. For example, if a certain temperature/irradiance profile during a certain amount of time is desired for a test specimen 46, the controller 102 can be programmed to adjust the position of the mirrors 35 so that the temperature/irradiance of the test specimen 46 closely follows the desired temperature/irradiance profile.

Furthermore, while the particular preferred embodiments have been shown and described, it will be obvious to those skilled in the art that changes and modifications may be made without departing from the teaching of the disclosure. The matter set forth in the foregoing description and accompanying drawings is offered by way of illustration only and not as limitation. The actual scope of the disclosure is intended to be defined in the following claims when viewed in their proper perspective based on the related art.

What is claimed is:

1. An accelerated weathering test apparatus of the type used to concentrate solar radiation upon at least one test specimen, the apparatus comprising: a target board operatively coupled to a reflector device; the target board configured to support at least one test specimen for exposure to concentrated solar radiation; the reflector device configured to reflect and concentrate solar radiation onto the at least one test specimen; and the reflector device including a bed and a plurality of mirrors, each mirror disposed on the bed in one of a first state, where solar radiation is reflected on the at least one test specimen, and a second state, where no solar radiation is reflected on the at least one test specimen, such that irradiance incident on the at least one test specimen from the reflector device is adjustable by movement of selected mirrors from the first state to the second state in response to an input in order to control one of a temperature of the at least one test specimen and the irradiance.

2. The apparatus as recited in claim 1, wherein the input is generated from one of the group consisting of a temperature sensitive component, an apparatus for replaying a recorded environment temperature cycle, an apparatus for generating a complex temperature cycle or a non-contact monitoring device.

3. The apparatus as recited in claim 1, wherein the input is an offset which adjusts for daily, and seasonal variations of the irradiance.

4. The apparatus as recited in claim 1, wherein the second state is selected from the group consisting of pivotally moving the mirror from the first state, removing the mirror from the first state and covering the mirror in the first state.

5. The apparatus as recited in claim 1, wherein each mirror is pivotally connected to the bed and operatively coupled to a device that facilitates movement of the mirror from the first state to the second state.

6. The apparatus as recited in claim 5, wherein the device is selected from the group consisting of a solenoid, linear actuator, motor, stepper motor, pneumatic actuator, hydraulic actuator or bi-metallic actuator.

7. The apparatus as recited in claim 5, further including a stop which orients each at least one mirror in the first state.

8. The apparatus as recited in claim 5, further including a controller operatively coupled to each device to selectively activate the devices to facilitate movement of the mirrors from the first state to the second state.

9. The apparatus as recited in claim 8, wherein the controller selectively activates the devices in response to the irradiance incident on a sensor.

10. The apparatus as recited in claim 8, wherein the controller selectively activates the devices in response to the temperature of the at least one test specimen.

11. The apparatus as recited in claim 8, wherein the controller functions to log activation of the devices and duration thereof to facilitate calculation of radiation exposure.

12. The apparatus as reeked in claim 1, wherein each mirror is connected to the bed at a fixed angle and operatively coupled to a device that facilitates covering of the mirror in the second state.

13. The apparatus as recited in claim 12, wherein the device is selected from the group consisting of a solenoid, linear actuator, motor, stepper motor, pneumatic actuator, hydraulic actuator or bi-metallic actuator.

14. The apparatus as reeked in claim 12, further including a controller operatively coupled to each device to selectively activate the devices to facilitate covering of the mirrors in the second state.

15. The apparatus as recited in claim 14, wherein the controller selectively activates the devices in response to the irradiance incident on a sensor.

16. The apparatus as recited in claim 14, wherein the controller selectively activates the devices in response to the temperature of the at least one test specimen.

17. The apparatus as recited in claim 14, wherein the controller functions to log activation of the devices and duration thereof to facilitate calculation of radiation exposure.

18. A method for adjusting irradiance incident on at least one test specimen in an accelerated weathering test apparatus of the type used to concentrate solar radiation upon the at least one test specimen in order to control one of a temperature and irradiance of the test specimen, comprising the following steps: fitting the apparatus with a target board operatively coupled to a reflector device, where the target board is configured to support the at least one test specimen, the reflector device is configured to reflect and concentrate solar radiation on to the at least one test specimen and the reflector device includes a bed with a plurality of mirrors; operatively coupling each mirror to the bed such that each mirror is independently disposed on the bed in one of a first state, where solar radiation is reflected on the at least one test specimen, and a second state, where no solar radiation is reflected on the at least one test specimen; and controlling a plurality of devices, where each device is operatively coupled to one mirror, with a controller to selectively activate the devices to facilitate movement of the mirrors from the first state to the second state in response to an input.

19. The method as recited in claim 18, wherein the input is generated from a device selected from the group consisting of a temperature sensitive component, an apparatus for replaying a recorded environment temperature cycle, an apparatus for generating a complex temperature cycle, and irradiance monitoring device or a non-contact monitoring device.

20. The method as recited in claim 18, wherein the input is an offset which adjusts for daily, and seasonal variations of the irradiance.

21. The method as recited in claim 18, wherein the second state is selected from the group consisting of pivotally moving the mirror from the first state, removing the mirror from the first state and covering the mirror in the first state.

22. The method as recited in claim 18, wherein each mirror is pivotally connected to the bed.

23. The method as recited in claim 18, wherein the device is selected from the group consisting of a solenoid, linear actuator, motor, stepper motor, pneumatic actuator, hydraulic actuator or bi-metallic actuator.

24. The method as recited in claim 18, further including the step of logging activation of the devices and duration thereof with the controller to facilitate calculation of radiation exposure.

25. The method as recited in claim 18, further including a stop which orients each at least one mirror in the first state.

26. An accelerated weathering test apparatus of the type used to concentrate solar radiation upon at least one test specimen, the apparatus comprising; a target board operatively coupled to a reflector device; the target board configured to support at least one test specimen for exposure to concentrated solar radiation; the reflector device configured to reflect and concentrate solar radiation onto the at least one test specimen; and the reflector device including a bed and a plurality of mirrors, each mirror disposed on the bed in one of a first state, where solar radiation is reflected on the at least one test specimen, and a second state, where no solar radiation is reflected on the at least one test specimen, such that a temperature of the at least one test specimen is adjustable by movement of selected mirrors from the first state to the second state in response to an input in order to control one of an irradiance incident on the at least one test specimen from the reflector device and the temperature.

27. The apparatus as recited in claim 26, wherein the input is generated from one of the group consisting of a temperature sensitive component, an apparatus for replaying a recorded environment temperature cycle, an apparatus for generating a complex temperature cycle, an irradiance monitoring device or a non-contact monitoring device.

28. The apparatus as recited in claim 26, wherein the input is an offset which adjusts for daily, and seasonal variations of the irradiance.

29. The apparatus as recited in claim 26, wherein the second state is selected from the group consisting of pivotally moving the mirror from the first state, removing the mirror from the first state and covering the mirror in the first state.

30. The apparatus as recited in claim 26, wherein each mirror is pivotally connected to the bed and operatively coupled to a device that facilitates movement of the mirror from the first state to the second state.

31. The apparatus as recited in claim 30, wherein the device is selected from the group consisting of a solenoid, linear actuator, motor, stepper motor, pneumatic actuator, hydraulic actuator or bi-metallic actuator.

32. The apparatus as recited in claim 30, further including a stop which orients each at least one mirror in the first operative position.

33. The apparatus as recited in claim 30, further including a controller operatively coupled to each device to selectively activate the devices to facilitate movement of the mirrors from the first state to the second state.

34. The apparatus as recited in claim 33, wherein the controller selectively activates the devices in response to the irradiance incident on a sensor.

35. The apparatus as recited in claim 33, wherein the controller selectively activates the devices in response to the temperature of the at least one test specimen.

36. The apparatus as recited in claim 33, wherein the controller functions to log activation of the devices and duration thereof to facilitate calculation of radiation exposure.

37. The apparatus as recited in claim 26, wherein each mirror is connected to the bed at a fixed angle and operatively coupled to a device that facilitates covering of the mirror in the second state.

38. The apparatus as recited in claim 37, wherein the device is selected from the group consisting of a solenoid, linear actuator, motor, stepper motor, pneumatic actuator, hydraulic actuator or bi-metallic actuator.

39. The apparatus as recited in claim 37, further including a controller operatively coupled to each device to selectively activate the devices to facilitate covering of the mirrors in the second state.

40. The apparatus as recited in claim 39, wherein the controller selectively activates the devices in response to the irradiance incident on a sensor.

41. The apparatus as recited in claim 39, wherein the controller selectively activates the devices in response to the temperature of the at least one test specimen.

42. The apparatus as recited in claim 39, wherein the controller functions to log activation of the devices and duration thereof to facilitate calculation of radiation exposure.

43. A method for adjusting a temperature of at least one test specimen in an accelerated weathering test apparatus of the type used to concentrate solar radiation upon the at least one test specimen in order to control an irradiance incident on the at least one test specimen, comprising the following steps: fitting the apparatus with a target board operatively coupled to a reflector device, where the target board is configured to support the at least one test specimen, the reflector device is configured to reflect and concentrate solar radiation on to the at least one test specimen and the reflector device includes a bed with a plurality of mirrors; operatively coupling each minor to the bed such that each minor is independently disposed on the bed in one of a first state, where solar radiation is reflected on the at least one test specimen, and a second state, where no solar radiation is reflected on the at least one test specimen; and controlling a plurality of devices, where each device is operatively coupled to one mirror, with a controller to selectively activate the devices to facilitate movement of the mirrors from the first state to the second state in response to an input.

44. The method as recited in claim 43, wherein the input is generated from a device selected from the group consisting of a temperature sensitive component, an apparatus for replaying a recorded environment temperature cycle, an apparatus for generating a complex temperature cycle, an irradiance monitoring device or a non-contact monitoring device.

45. The method as recited in claim 43, wherein the input is an offset which adjusts for daily, and seasonal variations of the irradiance.

46. The method as recited in claim 43, wherein the second state is selected from the group consisting of pivotally moving the mirror from the first state, removing the mirror from the first state and covering the mirror in the first state.

47. The method as recited in claim 43, wherein each mirror is pivotally connected to the bed.

48. The method as reeked in claim 43, wherein the device is selected from the group consisting of a solenoid, linear actuator, motor, stepper motor, pneumatic actuator, hydraulic actuator or bi-metallic actuator.

49. The method as recited in claim 43, further including the step of logging activation of the devices and duration thereof with the controller to facilitate calculation of radiation exposure.

50. The method as recited in claim 43, further including a stop which orients each at least one mirror in the first state.

* * * * *